United States Patent
Putnam et al.

(10) Patent No.: US 10,495,555 B2
(45) Date of Patent: Dec. 3, 2019

(54) FILTER-CARTRIDGE BASED FLUID-SAMPLE PREPARATION AND ASSAY SYSTEM

(71) Applicants: David Putnam, Sammamish, WA (US); Jason Putnam, Redmond, WA (US); Raymond Putnam, Sammamish, WA (US)

(72) Inventors: David Putnam, Sammamish, WA (US); Jason Putnam, Redmond, WA (US); Raymond Putnam, Sammamish, WA (US)

(*) Notice: Subject to any disclaimer, the term of this patent is extended or adjusted under 35 U.S.C. 154(b) by 602 days.

(21) Appl. No.: 14/510,104

(22) Filed: Oct. 8, 2014

(65) Prior Publication Data
US 2015/0096358 A1    Apr. 9, 2015

Related U.S. Application Data

(60) Provisional application No. 61/888,368, filed on Oct. 8, 2013.

(51) Int. Cl.
*G01N 1/40* (2006.01)
*B01L 3/00* (2006.01)

(52) U.S. Cl.
CPC ............ *G01N 1/4077* (2013.01); *B01L 3/505* (2013.01); *B01L 3/5023* (2013.01); *B01L 2200/0684* (2013.01); *B01L 2200/141* (2013.01); *B01L 2300/0681* (2013.01);
(Continued)

(58) Field of Classification Search
CPC ......... G01N 1/4077; G01N 2001/4088; G01N 2021/8571; G01N 2035/00475; G01N 2035/00485; B01L 3/5023; B01L 2300/0681
See application file for complete search history.

(56) References Cited

U.S. PATENT DOCUMENTS 3,023,750 A * 3/1962 Baron ................... A61J 1/10
128/DIG. 12
3,079,920 A * 3/1963 Bellamy, Jr. ............ A61J 1/10
604/409

(Continued)

*Primary Examiner* — Justin N Olamit

(57) ABSTRACT

The application relates to a device and method for preparing and testing a fluid sample using a filtration procedure for analysis of a filterable constituent of the fluid. In particular the process employs an enclosed pathway whereby the fluid sample may be put into a sealable flexible containment-vessel, and can then be passed through a fluid passageway to a removable enclosable filter cartridge, wherein the filterable constituent may be removed and the resultant filtrate fluid discharged from the cartridge. Once introduced to the flexible vessel, the enclosed pathway system thereby enables the fluid to be filtered and the filterable constituent examined with minimal complications of contamination of the sample through exposure to environmental pollutant external to the fluid sample.

A useful objective of the device and method is to enable analyses of microbiological content of a fluid sample.

The application further relates to a means of conducting the filtration of a fluid sample without necessarily requiring a pump or vacuum equipment to express or aspirate the fluid from the flexible containment vessel through the filter cartridge.

9 Claims, 4 Drawing Sheets

(52) U.S. Cl.
CPC ............... *B01L 2400/0644* (2013.01); *B01L 2400/0655* (2013.01); *G01N 2001/4088* (2013.01)

(56) References Cited

U.S. PATENT DOCUMENTS

| | | | | |
|---|---|---|---|---|
| 4,036,698 | A * | 7/1977 | Bush | C12Q 1/22 435/287.4 |
| 4,256,693 | A * | 3/1981 | Kondo | G01N 33/525 422/422 |
| 5,423,421 | A * | 6/1995 | Inoue | A61J 1/00 206/219 |
| 8,968,681 | B2 * | 3/2015 | Putnam | C12Q 1/24 210/436 |
| 2005/0221417 | A1 * | 10/2005 | Houghton | C12Q 1/22 435/34 |
| 2013/0071304 | A1 * | 3/2013 | Jeon | B01L 3/502753 422/502 |
| 2013/0270165 | A1 * | 10/2013 | Shevitz | B01D 63/02 210/151 |
| 2013/0288227 | A1 * | 10/2013 | Collins | C07K 16/2896 435/2 |
| 2014/0186828 | A1 * | 7/2014 | O'Hara | C12Q 1/6806 435/6.11 |
| 2015/0314285 | A1 * | 11/2015 | Cotton | B01L 3/502 435/30 |

* cited by examiner

FILTER-CARTRIDGE BASED FLUID-SAMPLE PREPARATION AND ASSAY SYSTEM

CROSS-REFERENCE TO RELATED APPLICATIONS

Related U.S. Application Data: Provisional application No. 61/888,368 filed on Oct. 10, 2013.

BACKGROUND

In the practice of testing fluid samples, for instance the analysis of microbiological organisms in pharmaceutical, beverage, or environmental fluids being good examples, it is important that the fluid sample be handled in a manner that prevents it from becoming contaminated or adulterated with organisms or other substances extrinsic to the sample that could alter the outcome of the microbial test. This includes introduction of organisms from the external environment. A prime example is the testing of sterility of a parent fluid volume by removing a portion as a test sample. If the extracted fluid sample becomes contaminated in the analytical process through exposure to organisms that are not part of the parent fluid, then the outcome of the test will be flawed.

For testing purposes, it can be necessary to obtain the sample at one location that is the source of the parent fluid volume, and then convey the sample to another locale where the testing process takes place, such as in a test laboratory. This requires samples to be securely sealed in a vessel suited for transport, which will not leak, nor allow the contents to become contaminated in the transportation process. The fluid sample volume can vary in amount from microliters to liters, 100 mL being an exemplary volume for testing the microbial content for instance of water for human consumption.

Commonly used fluid sample vessels are glass and plastic bottles, usually sterilized for test applications involving the microbiological analyses. These have the disadvantage that their weight and typical rigidity make them costly to transport, and inconvenient to pack, ship and store. An alternative to this is a collapsible or flexible thin wall plastic containment vessel, a preferred case being in the form of a pouch or bag. The pouch or bag has the advantage of low cost, light weight, and space-saving for compact packaging. One bag design that is frequently used as a fluid sample vessel, called Whirl-Pak, employs a twisted-wire top closure that addresses the problem of creating a leak-proof seal for the filled container, without requiring a cap or fixed closure for the opening where the sample fluid is introduced.

Whether involving either rigid or flexible vessels, the container used for the initial collection, transport, and storage of the fluid, ultimately is opened in order to access the sample and remove all or some portion of the fluid upon which the analytical procedure is then performed. The opening of the vessel and the operation of extricating fluid for testing exposes the sample to the potential contaminants external to the vessel and the fluid sample.

For microbiological testing, one prevalent test type is a filtration process in which the sample is aspirated under vacuum through a porous membrane that captures the bacteria and removes the fluid. The procedure typically involves transferring fluid from the fluid-sample vessel to a filter-apparatus that consists of a vessel capable of holding the volume that is to be processed and a membrane filter (MF) constrained therein through which the fluid will be suctioned. The membrane filter is then exposed to bacterial-growth media and incubated in a culture vessel, which typically involves a physical manipulation of the MF to convert it from being in the filtration-processing state to being in an incubation condition.

An advantage offered by the membrane-filter assay method with respect to microbial analyses is that individual organisms can be captured from relatively large volume fluid samples and they can be cultured on or in the filter when it is exposed to a suitable growth medium and incubation temperature. The organisms proliferate and eventually form colonies that can be identified on the filter surface. The colony formations can be differentiated by bacterial type, and enumerated, thereby providing valuable information about the concentration of the parent organisms present in the fluid sample at the time of its filtration.

These sample-preparation procedures, from the point of getting fluid out of the fluid sample vessel, through the filtration process, and additionally into the assay and culture phase of analysis, involve a variety of manipulations on the part of the user. There are attendant opportunities for contamination through exposures of the fluid sample, or the substance removed from it, by the filtration process and the steps of preparation for the assay and incubation. Moreover, special equipment is needed and skilled personnel (trained in its usage as well as the laboratory procedures typically employed to minimize the risks of external contamination) are required. A significant amount of materials are used that come in contact with the sample, which after use must be treated as contaminated thereby either disposed of or disinfected, or both.

For these and other reasons, the analytical procedure is therefore typically performed in the clean environment of a well-equipped microbiological test laboratory. However, access to a lab setting and trained operators is often not practical and presents complications towards testing samples in many cases.

SUMMARY OF THE INVENTION

The present device and method provide innovative solutions to the problems identified that hinder sample preparation and testing and are often associated with limited resources, economics, transportation, or timing logistics. The device and method offer the advantages of:

Preventing contamination of the fluid sample

Attain compact size, low weight, and low cost of the sample-preparation system used to hold and filter the sample Simplify the procedure so that unskilled people can perform the filter-processing of a fluid sample and analyze the filterable constituent Prepare the filtered sample with a finite volume of the fluid sample Enable rapid, simple, efficient filtration of the fluid without involving the necessity of a pump or a vacuum system or electrical power Enable a membrane-filtration based microbiological assay that may be performed outside a laboratory without incubation equipment The method and device of the invention each have several aspects operating as a system, no single one of which is solely responsible for its desirable attributes. Without limiting the scope of this invention, its more prominent features will now be discussed briefly.

The present invention provides a device and method for holding a fluid sample, processing it by filtration, and conducting analysis of a filterable constituent which may be extracted from the solution, thereby concentrated, with removal of the fluid filtrate solution. This can be done in a manner employing a device having a closed fluid-pathway that prevents contamination of the sample.

The device constitutes an integrated enclosed fluid-pathway system comprised of a collapsible, sealable, flexible fluid sample containment vessel with a removable enclosable filter cartridge. The vessel and filter cartridge can be connected by an enclosed fluid conduit.

The method of the present invention can comprise:
1. Introducing a fluid sample into an opening of the fluid-sample containment vessel; and
2. Sealing the opening; and
3. Passing said fluid sample from the containment vessel to the attached filter cartridge by way of an outlet on said vessel and through an enclosed fluid conduit to said filter cartridge; and
4. Extracting a filterable constituent from the fluid sample within the filter cartridge; and
5. Discharging the filtered fluid from said cartridge through an outlet; and
6. Removing the filter cartridge and the extricated fluid-sample constituent from the fluid-pathway;
7. Performing an analysis of said filterable constituent within the filter cartridge, which can be enclosed, to measure the presence or amount of a constituent of the fluid sample collected by said filter cartridge.

The fluid sample containment vessel preferably constitutes a flexible container which can collapse when empty, or expand to accommodate filling with fluid and gas. It is sealable, to prevent potential contamination of the contents by exposure to the external environment and to enable transport without loss of the fluid sample. Flexibility of the vessel is advantageous, so when containing fluid, the vessel can collapse thereby allowing discharge of its fluid and gas contents through the fluid-pathway, since the vessel's internal pressure differential equalizes. This approach avoids the need to open the vessel in order to remove fluid-sample for filtration, and also avoids requirements to vent the vessel in order to relieve negative pressure within it caused by fluid outflow.

The fluid sample containment vessel can contain pre-administered reagents, chemicals, media or materials that are to be delivered through the fluid pathway separately or in conjunction with the fluid-sample that the user introduces to the vessel at the point of use.

The flexible nature of the fluid containment vessel is important to the inventive aspect of enabling external pressure to be applied to the outside of the vessel in order to cause fluid, or gas, to be forced under positive pressure to pass from the containment vessel and be driven through the filter cartridge.

The device and method of the present invention further provide a capability to control, regulate, and limit the amount of fluid that is filtered. The fluid-pathway for passing fluid from the containment vessel to the filter cartridge can be preferably closed or blocked to thereby occlude passage of fluid from the vessel into the cartridge prior to the time chosen to filter the fluid. The occlusion of the fluid pathway can be removed, or reestablished, at chosen times to allow or alternatively stop fluid flow from the containment vessel without breaching the integrity of the enclosed fluid pathway or exposing the fluid sample to external contamination.

The filterable constituent contained within the fluid sample can be bacteria, cells, organisms, particulate, or other substance dissolved or suspended in the fluid sample which can be collected by some means of separation of the constituent from the fluid phase that is preferably removed. The filtration means include porous membrane filters, and physical, chemical, or magnetic or electrical mechanisms for entrapping, binding, or otherwise extracting, retaining, and separating the filterable constituent from the filtrate fluid which is removed.

The filter cartridge may constitute a removable component of the system that can be detached from the fluid-pathway and its connection to the fluid containment vessel. The filter cartridge may be enclosed or enclosable with respect to being by itself a standalone component that can be sealed. The filter cartridge may also contain agents or reagents disposed within it that can be involved in the analytical assay procedure including, for example, culture of the filtered constituent.

The filter cartridge can protect and prevent exposure of the cartridge's contents, including the fluid or the filtration means, to external contaminants outside of the fluid-pathway. The filter cartridge may have a fluid inlet and a fluid outlet that are parts of its integral enclosed fluid-pathway. The inlet can connect to the enclosed fluid conduit that conveys fluid from the containment vessel. To prevent exposure of the fluid content to the environment external to the cartridge, either or both the cartridge's inlet and outlet can be sealed with enclosures, and additionally can have a tortuous path that protects the contents of the cartridge.

The fluid-pathway and filter cartridge can allow the passage of air (or gas) trapped within the containment vessel, to be intentionally or unintentionally passed through the fluid-pathway and/or the inlet of the filter cartridge. The fluid-pathway can additionally provide for the escape or release of air entering the cartridge so that the air will not block the subsequent introduction of: sample fluid into the cartridge; liquid reagent for conducting the analytical testing; and/or analytical medium for cell-culture.

The filter cartridge can be pre-assembled to the fluid conduit, thereby connected to the fluid containment vessel, when the vessel is filled with the fluid sample. The filter cartridge may also be removable from the fluid-pathway. After the fluid sample has been processed through the filter, the filter-cartridge can be detached to facilitate the contents of the cartridge being subjected to analytical procedures, incubation, and examinations, independent of the other components of the system.

The filter-cartridge may be fitted with a removable cover or closure of its fluid pathway at the outlet terminus. This can protect the cartridge and the fluid-pathway from external contamination as well as enable control over movement of fluid in the pathway and prevent leakages.

This fluid-sample preparation device and method is applicable and valuable towards performing membrane-filter based tests of microorganisms which utilizes an enclosed and protected technique and enables analysis of filterable-constituent within the cartridge.

It is novel because its simplicity enables unskilled users to reliably process fluid-samples in the field by filtration, at the time and place of sample acquisition without accidental external contamination. Moreover, it is enabling execution of in situ analyses of the cartridge contents, which include the identification and enumeration of microbes in a more efficient manner that does not require laboratory equipment such as vacuum systems, pumps, and incubators.

BRIEF DESCRIPTION OF THE FIGURES

The above mentioned and other features of the invention will now be described with reference to the drawings of a preferred embodiment of the present invention. The illustrated embodiment is intended to illustrate and not to limit the invention. The drawings contain the following figures.

DETAILED DESCRIPTION

The Device:

This invention provides a system for collecting, holding, transporting, and the delivery of a fluid sample in a sealable flexible containment vessel which enables discharge of the fluid, and air or gas entrapped in the vessel, through an enclosed fluid-pathway to a removable enclosable filter-cartridge that collects and concentrates constituents from the fluid. This fluid sample-preparation system enables analyses to be performed on the filterable constituents contained within the cartridge with little risk of the fluid sample, specifically that which is filtered out of the fluid in the cartridge, from being contaminated or adulterated by exposure to the environment outside of the system. The force causing the fluid discharge from the vessel and through the cartridge can be from at least one of the means of a positive-pressure exerted upon the outside of the flexible vessel, or by negative-pressure applied to the distal end of the fluid path on the outlet side of the filter cartridge. The application of a positive-pressure includes means which utilize gravity and atmospheric pressure or a pressure from the hand.

Figure 1:
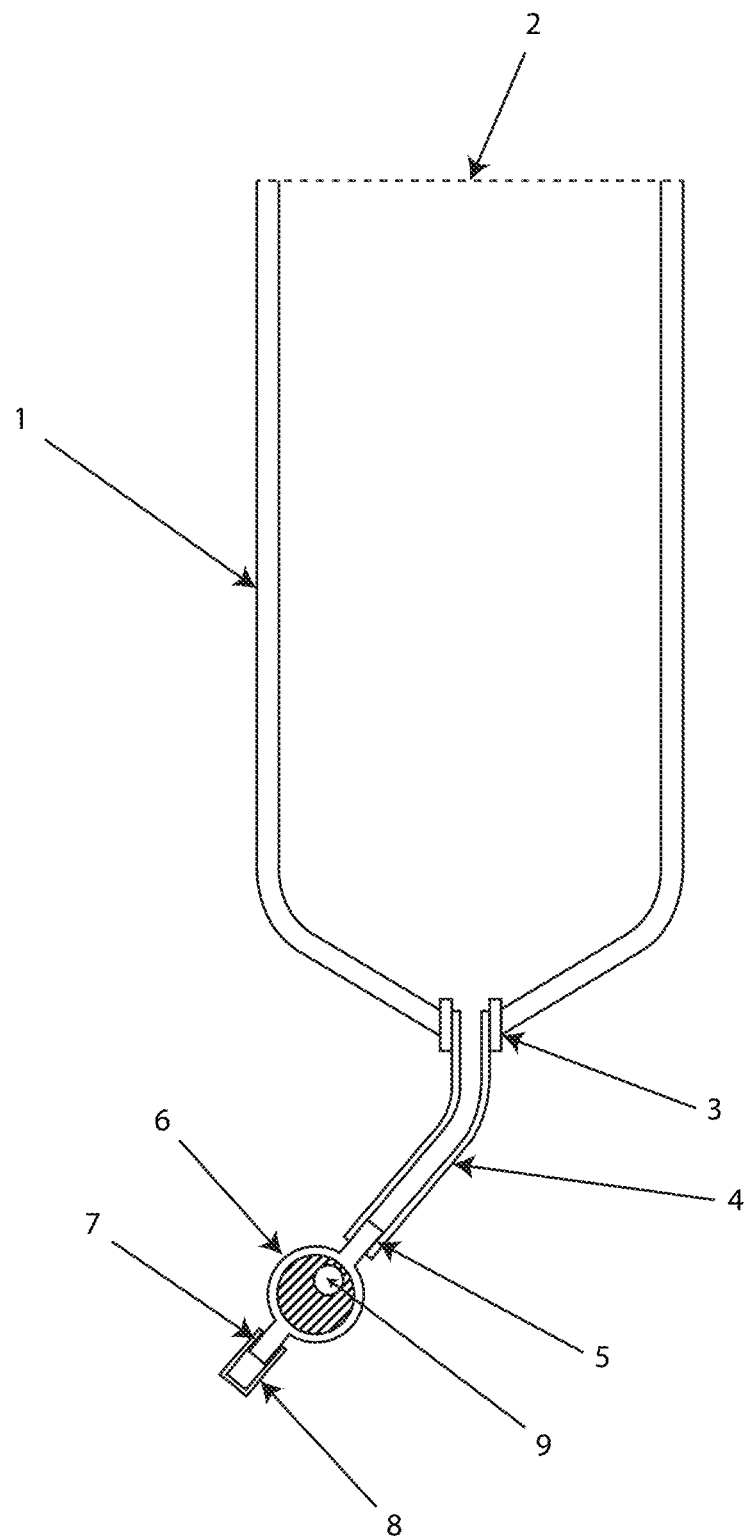
FIG. 1 shows an overview of the primary sample-preparation device components.

The main system components of the device, as shown in the FIG. 1 overview, are a fluid-sample containment vessel 1, an enclosed fluid conduit 4, which connects the vessel to a removable enclosable filter cartridge 6. Additional elements illustrated are the flexible fluid sample containment vessel 1 having a fluid inlet 2 which is open and uncovered. The containment vessel has a fluid outlet 3, providing for an attachment which is shown connected to an enclosed fluid conduit 4. A filter cartridge 6 has an inlet 5 which connects in removable manner to the fluid pathway of the conduit 4. The cartridge has an outlet 7, which in FIG. 1 is the terminus of the enclosed fluid pathway and the point of discharge of fluid out of the filter cartridge. The outlet is capped or plugged with a removable cover 8. This illustration shows a filter cartridge having a vent 9 which permits gas to escape from the inside of the cartridge.

The fluid containment vessel in a preferable embodiment is a flexible thin-wall collapsible bag or pouch, which is compressible when empty in a manner thereby enabling it to be flattened, folded, or rolled for convenient compact storage and shipping. The vessel provides an opening 2 for introducing the fluid sample. Preferably the opening is sufficiently large, for instance ¼ inch or more, such that fluid can be readily introduced, for instance by pouring sample in, without requiring additional equipment like a filling machine, a funnel, or a syringe injector, to get the fluid sample into the vessel, especially without contamination. The vessel, owing to its flexible nature of its sides or walls, expands to accommodate the filling with fluid.

The flexible fluid containment vessel is sealable to prevent external contamination. The seal of the opening through which the sample fluid is introduced can be in the form of a cap or plug, a zip-lock seal, a roll-up seal, or other closure of a type effective for containment of a fluid in a vessel. The containment vessel opening is preferably closed and kept closed, capped, or sealed, prior to the introduction of the fluid-sample in order to protect the internal aspects of the vessel from contamination. One embodiment is shown in FIG. 2, which illustrates a removable plastic tab, intact, covering the opening 2 at the upper end of the vessel.

Figure 2:
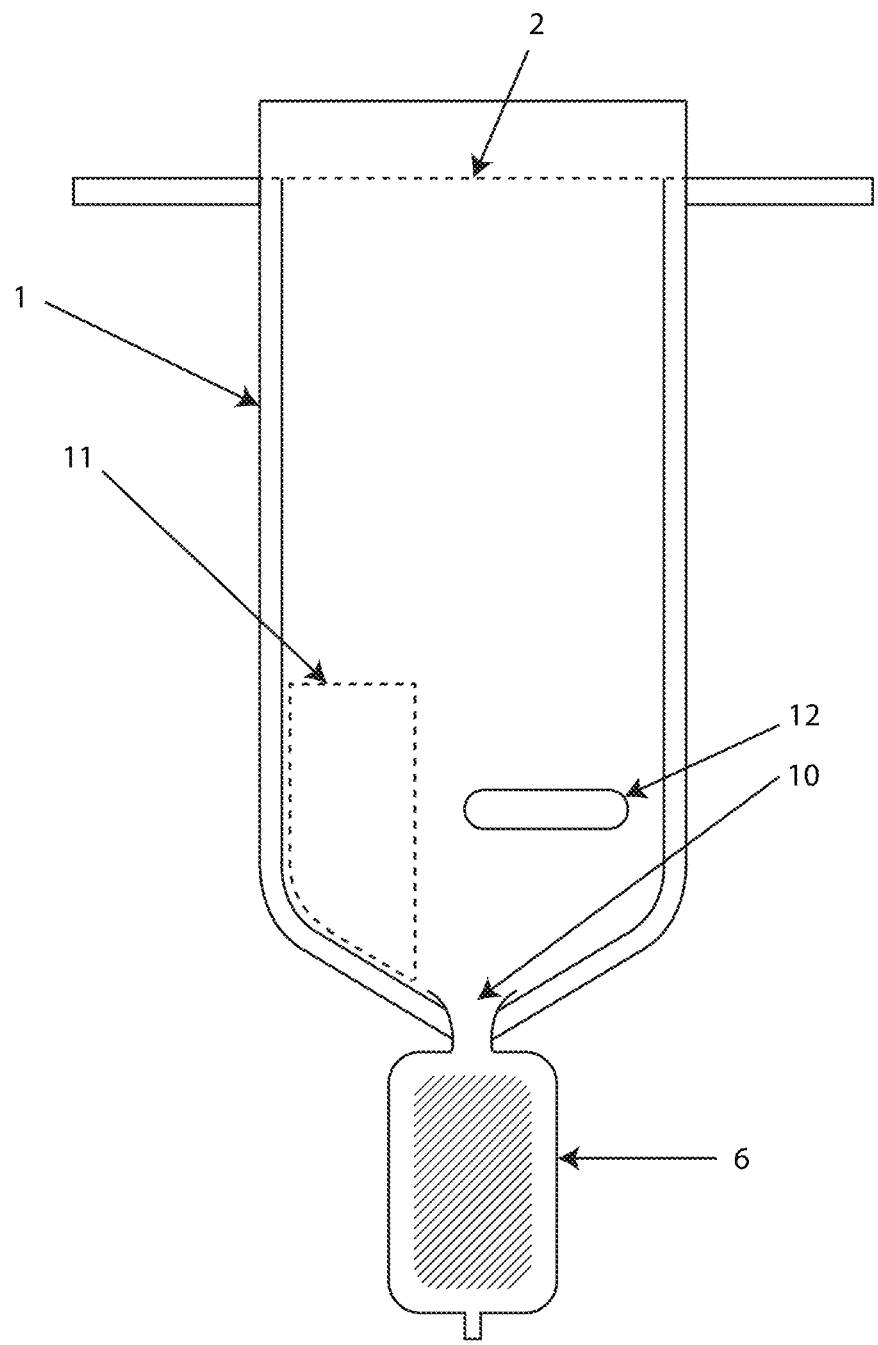
FIG. 2 shows an arrangement where the flexible containment vessel is connected directly to the filter cartridge via a large outlet.

FIG. 2 shows an arrangement where the flexible containment vessel has an intact tear-away tab covering over the opening 2 of the vessel 1. It also illustrates a configuration where the outlet of the vessel and the inlet of the filter cartridge 6 are both sufficiently large openings and directly attached 10 in a manner that can allow gas to escape from the cartridge back into the vessel 1. FIG. 2 also illustrates a scenario where there is no need for a fluid conduit to effect a connection between vessel 1 and filter cartridge 6 and establish an enclosed fluid pathway.

After sample fluid introduction, in the case of the vessel consisting of a flexible bag or pouch, the opening can be sealed by rolling, folding, or clamping the vessel-wall material so as to create a leak-proof closure. An example of this is the approach used in Whirl-Pak products. They have a perforated, tear-away tab on the top of the bag which is removed to create the opening for access to the inside of the bag. After putting in sample fluid, two wires encircling the opening at the top of the bag are used to twirl or roll-up the open end of the bag and form a tight seal which cannot unwind after the wires are twisted together.

The fluid-sample containment vessel can contain inclusions within it which are substances, agents or reagents, or media, that are packaged in a manner to be delivered through the fluid pathway separately or in conjunction with the fluid-sample. The inclusions can include sample-preparation processing aids or materials to facilitate the analytical process. One category of embodiment are inclusions that are added at the point of production and assembly of the inventive device. To prevent contamination of the fluid-sample, inclusions can be added that are clean, or sterile, or can be sterilized after addition to the device.

One example of a sample-processing aid to be pre-packaged in the containment vessel is a swab or sponge inclusion, for acquisition and preparation of the fluid-sample. After removing the swab from the containment vessel and using it to swab-test a surface for bacteria, it could be put back in the vessel along with the sample fluid. The fluid would serve to elute the bacteria from the swab. The fluid containing the bacteria can then be processed by filtering through the filter cartridge which captures the bacteria enabling the microbial analysis.

Another type inclusion is a bacterial-culture growth media, for example as a dehydrated agent that is incorporated inside the vessel. The agent is subsequently rehydrated by the fluid-sample that the user may introduce to the vessel at the point of use. The dissolved agent thereby gets passed through the fluid-pathway with the filtration processing of the sample.

Inclusions to be placed or incorporated into the fluid containment vessel can themselves be packaged in a manner such that their delivery to the fluid-pathway involves a manipulation or processing that can be performed within the flexible vessel, without requiring the vessel to be opened. Thereby the integrity of the enclosed containment vessel is maintained and external contamination avoided. An example is the inclusion of an agent, such as a culture media, that can be packaged within a breakable or dissolvable capsule which is incorporated into the vessel. Such an inclusion of a capsular form 12 is represented in FIG. 2. The inclusion indicates a fracturable ampule 12 within the containment vessel.

The fluid-sample containment vessel can also have special structural inclusions consisting of functional modifications to its internal aspects integrated to facilitate vessel's role in sample preparation. The inclusion can serve to aid retention, or delivery, of the fluid-sample contents of the vessel, or utilization of any other inclusions incorporated into the vessel. Internal modifications include walls, baffles, or separatory dividers within the vessel. Such can be used to create internal sub-compartments, chambers, or partitions, inside the vessel.

Such subdivisional compartments within the vessel can be open-ended, exposed to the fluid-sample, as illustrated in FIG. 2 by the internal sub compartment 11 formed between the walls of the vessel. Alternatively such inclusions can be sealed from the fluid, constituting a self-contained enclosure within the containment vessel. An inclusion that is enclosed inside the vessel can be made intentionally rupturable for instance by the user pressing on the vessel wall to release or activate an agent. Another embodiment can be a sub-compartment implemented into the vessel to receive a specific portion of the fluid-sample volume, and it could further be employed to retain a media or reagent capsule within it.

Figure 4:
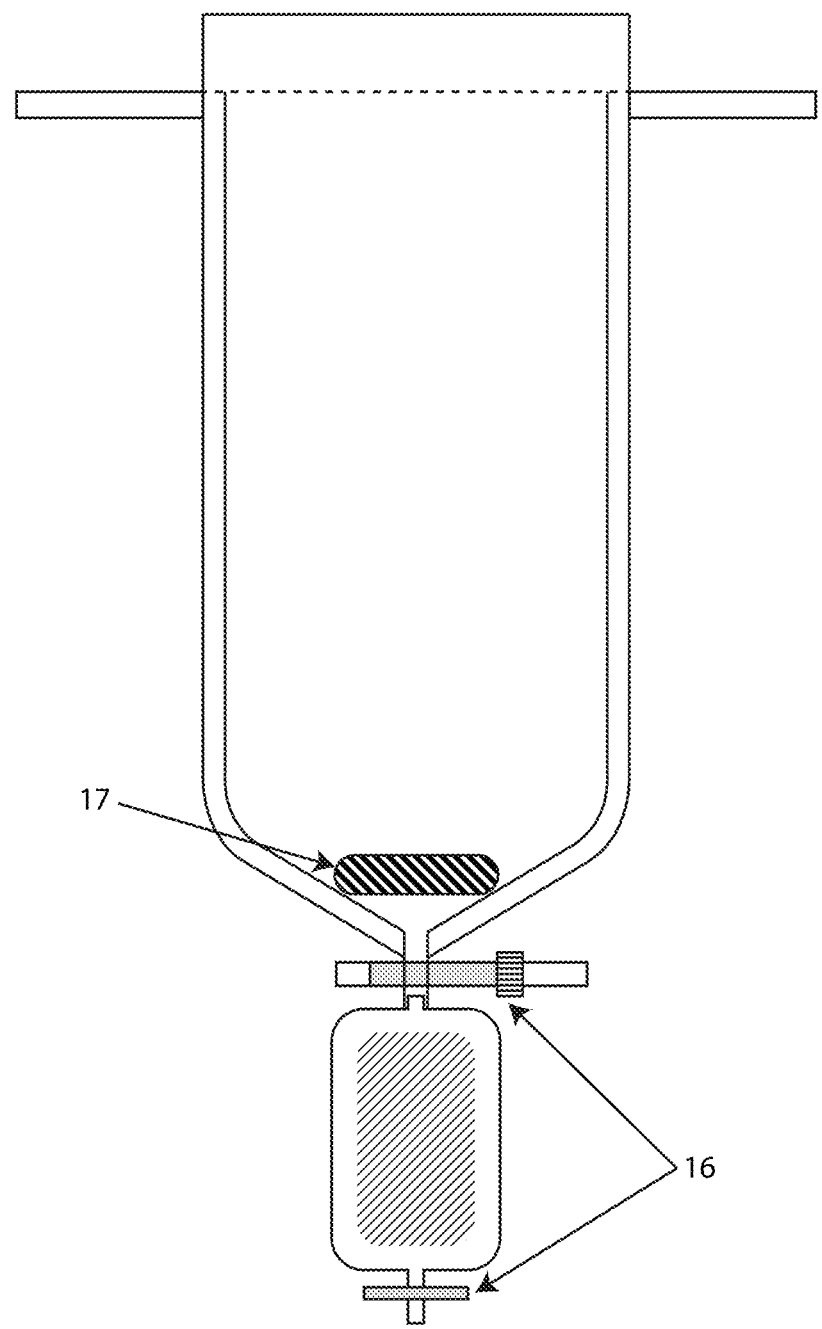
FIG. 4 shows an embodiment of fluid control mechanisms and an inclusion as a pre-filter.

Another embodiment of an inclusion internal to the containment vessel constitutes a component that plays a physical role in the sample preparation and analyses of the filterable fluid constituent. An example is the incorporation of a pre-filter element or a porous matrix or other material which prevents unwanted substance in the fluid-sample from entering the devices fluid-pathway. Such an inclusion is illustrated in FIG. 4 as a pre-filter 17 could reduce interference with the sample processing, filter plugging, or the analysis of filtered constituent in the filter-cartridge.

The size, shape and volume of the containment vessel can be variable, determined by the application, inclusions or integrations of sample processing agents or aids, and the volume of sample fluid that needs to be processed through the filter-cartridge for the analytical procedure. A volume of 100 milliliters is common. Alternatively the volume can be very small, such as one milliliter, or quite large, as in liters.

In one embodiment the vessel contents can be viewed to ascertain the amount and properties of the fluid sample, such as its color. One option may be that the level of the top of the fluid sample is discernable. The vessel may have one or more volume-indicator markers on it so that the amount of fluid contained in the vessel can be ascertained based on viewing the fluid level in the vessel. Thereby the vessel can be filled to contain a definitive amount of sample fluid. Indicator mark(s) can also enable a user to gauge and control the discharge of a definitive volume of fluid sample out of the vessel.

The vessel has an outlet 3 that allows the discharge of a fluid-sample from the vessel. The outlet consists of an aperture, with a fitting to which the enclosed fluid conduit 4 connects in one embodiment. The outlet can be incorporated into a wall of the vessel, and located in a manner such that the fluid sample may flow by gravity out of the vessel, as illustrated in the embodiment of FIG. 1. The outlet can alternatively be located on any wall of the vessel.

Another option can also be an implementation of the outlet into the vessel's closure mechanism, e.g. a cap or plug, used to seal the opening whereby fluid is introduced into the vessel. In this manner, the vessel need only have one opening through which fluid is introduced, and a closure thereof which incorporates the outlet aperture through which fluid flows out of the vessel to the filter-cartridge.

The outlet can further constitute an opening made sufficiently large to enable both fluid, and air including air bubbles, to pass freely both in and out of the containment vessel through the outlet and the fluid path joining it with the filter cartridge. Likewise such embodiment allows air and air bubbles carried into the filter cartridge to escape from it and pass through the fluid pathway such that the air does not block the fluid flow through the filter cartridge. Such sufficiently large outlet is depicted in FIG. 2, 10.

The enclosed fluid conduit 4 provides a connection between the vessel outlet 3 and the removable filter cartridge 5, and it enables protection from external contamination of fluid-sample exiting the vessel and passing to the filter cartridge. It can establish a flexible pathway to the cartridge. A tubing component is an example. In different embodiments it can be an extension of the vessel, or an extension of the inlet 5 of the removable filter-cartridge 6; in either case providing a protected enclosed fluid-pathway between the vessel and cartridge. In some embodiments there may be a direct attachment of the filter cartridge to the containment vessel, in which case the extension as a fluid conduit component is superfluous, as depicted in FIG. 2.

Figure 3:
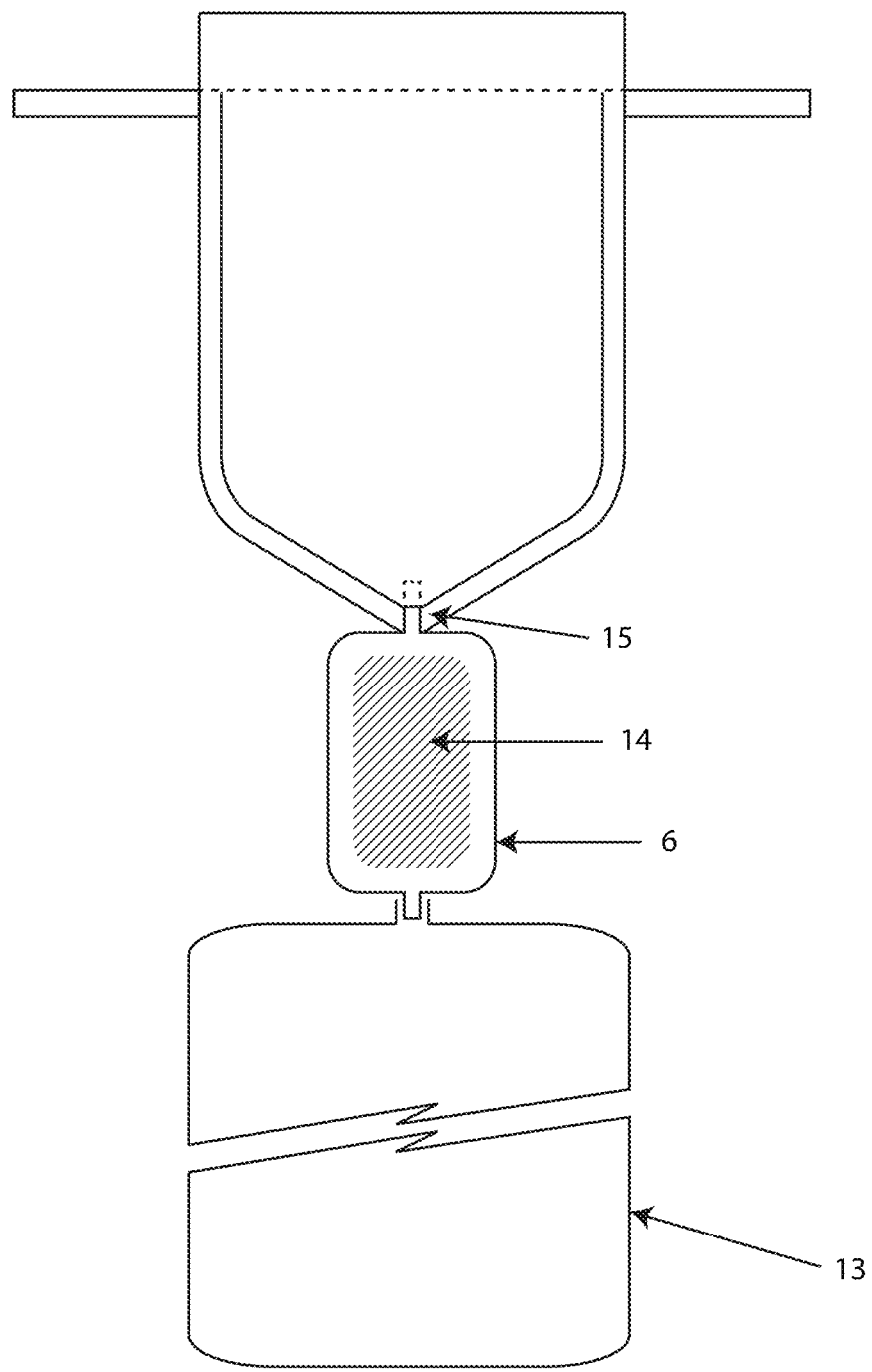
FIG. 3 illustrates a fluid path situation in which the filter cartridge has attached to its outlet a discharge collection vessel.

In alternative embodiments the fluid flow out of the vessel through the pathway to the filter cartridge can be controllable so that it can be started or stopped or regulated at will. FIG. 3 shows a fluid control mechanism consisting of a push-pull valve 15 implemented at the point of connecting the containment vessel and the filter cartridge. To achieve this regulation, a flow-control means can be further incorporated: (a) at the level of the enclosed fluid conduit; (b) at the vessel outlet; or (c) within the vessel, before fluid gets to the outlet, as shown in FIG. 4, 16.

The means for controlling fluid-sample flow is achieved through various approaches that provide a blockage or occlusion at one or more parts of the fluid-pathway, such as using an in-line valve, or a device that plugs or compresses the fluid conduit to restrict flow, or a clamping mechanism external to the fluid-pathway that enables the fluid flow to be stopped. A clamp 16, for instance and shown in FIG. 4, applied either to a flexible vessel on the upstream side of the filter cartridge inlet, or to a compressible flexible fluid conduit on the downstream side of the filter cartridge outlet, constitute practical control means.

An alternative approach to controlling flow is to orient the vessel and fluid-pathway such that gravity does not allow the fluid sample to contact the outlet, or to flow through the fluid-pathway of the system. This can be simply based on elevating the outlet or any portion of the fluid-pathway above the level of fluid sample in the vessel. It is of significance that the inventive design and method advantageously accommodates the fact that some air or gas will be enclosed in the fluid-sample containment vessel after the fluid is introduced and the vessel opening is sealed closed. Reorienting the vessel, the outlet, and/or the fluid-pathway to the filter-cartridge can optionally allow fluid-sample to reach the outlet and enable gravity to play a role establishing fluid flow through the pathway.

Another fluid control embodiment takes advantage of the outlet cover 8 provided at the distal end of the outlet of the filter cartridge. Having the outlet cover in place blocks the fluid-pathway and thereby constitutes a fluid-flow controlling means. The procedure for using the inventive device can employ the outlet cover as a means to control a hydraulic lock on the fluid pathway, which thereby restricts or prevents fluid movement in the pathway.

The filter cartridge as shown in FIG. 1, 6 in one embodiment may comprise a housing that contains the filtration means and prevents external contamination of it, as well as the fluid-sample which passes through the housing to remove filterable constituents. The cartridge has an inlet 5 and an outlet 7 for fluid-sample passage. The inlet 5, which receives the inflow of fluid-sample from the vessel 1 is attached to the vessel via connection with the enclosed fluid conduit 4.

The inlet 5 and the outlet 7 can be reversibly attached or detached from the other components of the fluid pathway system. In one embodiment, the inlet of the filter cartridge can extend from the housing of the filter cartridge such that it mates with the containment vessel outlet 3 in an attachable, detachable manner, and constitutes the enclosed fluid conduit. As previously described, one embodiment has the inlet to the filter cartridge sufficiently large that air getting into it can escape back out of it, for instance to avoid air blockage of fluid flow into the cartridge. FIG. 2.

The filter means in the cartridge is interposed between the inlet and outlet of the filter cartridge such that the fluid-sample to be filter-processed passes over or through the filtering means, so as to facilitate removal of the filterable constituent. The housing distributes fluid-sample over the filtration means and also collects filtrate that has passed through the filtering means, which resides between the incoming and outgoing fluid. The filter cartridge can thereby be effectively described as being partitioned with inlet and outlet sides with respect to its fluid pathway. The respective inlets and outlets in a preferred embodiment of the cartridge will utilize a "tortuous" or convoluted pathway for either or both, so as to protect them from external contamination whenever they are not explicitly enclosed or covered.

The filtration means that can be contained within the filter cartridge, as illustrated in FIG. 3, 14, may constitute a porous membrane filter, and for example have porosity appropriate for removing bacteria and other organisms from the fluid-sample. Membrane filters as used for microbiological assays can be selected from a variety of well-known candidates made out of such representative materials as mixed-cellulose ester, polyether-sulfone, cellulose-acetate, polycarbonate, nylon, glass and paper fibers. The porosity rating can range from typically 0.2 to 1.2 microns, though larger and smaller pore sizing and matrices made from other media as known to those skilled in the practice of filtration may employ to best serve the application of the device.

An example of filter-cartridges in the category that can be implemented as a component for use in the inventive device are in-line filter products made by medical device manufacturers to prepare clarified or sterile-filtered fluids. In particular, an embodiment can employ a filter cartridge that is vented at its fluid inlet side. The vent may serve to allow air to escape from within the cartridge and at the same time prevent external microbial contaminants from entering the cartridge. Venting of the cartridge, with protection of the contents, such as through use of microporous bacterial-barriers or gas permeable material, is also a further embodiment. A vent, such as depicted in FIG. 1, 9 allowing gas exchange between the inside of the filter-cartridge and the outside environment can enable the exit of air from the filter cartridge.

Other physical, chemical, or magnetic or electrical mechanisms for entrapping, binding, or otherwise extracting, and retaining the filterable constituent from the filtrate fluid can be implemented consistent with there being a retentive mechanism for separating a constituent from the fluid sample that passes through the filter cartridge.

The filter cartridge may provide a housing employing surfaces enabling the filter within it to be visually observed by eye, or examined with the aid or a microscope or other instrument, and/or analyzed with equipment for interrogating the contents of the cartridge. This is important to the analytical process which uses the invention as a fluid sample-preparation and assay device enabling interrogation of the cartridge content with testing of the filterable-constituent involving visual examination and optical analyses. For example, to conduct microbial analyses involving membrane-filter based culture assays, a transparent surface above the membrane whereon colonies grow making them viewable by eye or optical instrumentation is a preferable embodiment.

One embodiment is to have the filter cartridge small in size, internal volume and thickness. Such cartridge as can be placed and held next to the body may permit it to be exposed to the warmth of the body. This enablement, for purposes of incubation, for instance allows microbiologic assays to be conducted involving culture of organisms, such as *E. coli*, whose growth is promoted at or near 30-37 degrees C. Other embodiments of filter cartridges large in size or volume and diverse in shape and form can be created for different applications as will be appreciated by those skilled in the practice of fluid filtration and are to be regarded as consistent with the presently described device and method.

The outlet 7 of the cartridge consists of an enclosable pathway for the discharge of fluid which has been filtered. The outlet can be a physical extension of the filter-cartridge 6 housing. Optionally the outlet can also embody an outlet extension associated with it, such as a segment of tubing. An outlet extension can provide a means of having the filtrate fluid discharge at a distance from the cartridge.

An outlet cover or plug 8 is a component of the system that can be reversibly attachable, detachable, at the distal end of the fluid-pathway. Preferably it mates in a leak-proof manner with the outlet 7 of the filter-cartridge, or with the terminus of an outlet extension if such is installed at the outlet. The closure can serve several functions: (1) It prevents external contaminates from entering the fluid-pathway and the internal aspects of the system via the distal outlet before the device is used for fluid-sample preparation or analysis. (2) It provides a fluid flow control-means by blocking passage of fluid or air through the filter-cartridge when it is attached to the outlet of the cartridge; and accordingly must be detached in order to allow fluid to flow through the system and discharge out of the cartridge. (3) When installed to create a closure at the outlet/discharge point, after fluid-sample and analytical reagents have been applied to the cartridge, the cover or plug hydraulically locks fluid in the filter cartridge, and prevents leakage, and prevents ingress of external contaminates.

A vacuum, or negative-pressure, can be applied to the outlet/discharge terminus at the distal end of the system's fluid pathway to utilize suction for drawing fluid through the fluid-pathway via aspiration. The vacuum can be derived from typical fluid or vacuum pump based equipment, or more simplistically by connecting such as a syringe or squeeze-bulb type apparatus to the fluid-cartridge outlet.

The volume of fluid that is passed through the filter-cartridge can be controlled at either the inlet side of the cartridge or the outlet. Several means of controlling the flow in that fluid pathway have been previously described. Additionally, detachable components can be applied at the distal end of the fluid pathway in order to control and regulate the fluid flow through the filter-cartridge. Examples of such embodiments but not limited to these are: (a) attaching a fluid-collection device to the cartridge's outlet that allows the user to determine the volume of fluid that has been processed and stop the flow after collection of the appropriate amount; or (b) attaching a collection device that stops the flow itself. An example of the latter as shown in FIG. 3 can be the attachment of a collapsible bag or pouch 13 that is only able to receive a finite fluid volume, thereby preventing further fluid flow after it is filled with a designated volume of the system's discharged filtrate fluid.

Method of Use

To use the device, the fluid-sample containment vessel is opened by the user and the fluid-sample is introduced within. The amount added can be limited to the appropriate volume needed to meet requirements associated with the analytical application to be performed on the fluid-sample. Additionally, application-specific substances, agents or reagents, culture media, powders or liquids, and other sample-preparation aids to testing can also be added as necessary. After the introduction, the vessel opening is sealed. The vessel may have some air or gas entrapped within it as a headspace.

After the filling and sealing, access to the vessel through the opening may no longer be needed. Subsequent discharge of fluid-sample can be through the vessel outlet and the enclosed fluid-pathway. Once sealed, the integrity of the vessel thereafter does not have to be subsequently breached and the contents are not put in jeopardy of external contamination through opening the vessel and exposing its contents. Ensuring that a vessel's integrity has been maintained in a chain-of-custody and that the fluid-sample contents have not been adulterated is an important value of the device.

With the fluid sample in the containment vessel, the flow of fluid from its outlet and through the fluid pathway can be blocked or regulated by the utilization of one or more of the means for controlling fluid-sample flow that we have described or otherwise approaches consistent with flow-control mechanisms familiar to those skilled in the art. This can be the preferential state for keeping the fluid-sample in the vessel for a time prior to its filtration. Constraining the fluid to the vessel may be preferred in various cases, for instance, to allow time for an agent associated with the analytical procedure to react, e.g. the dissolving of a thiosulfate tablet to dechlorinate a water sample. It can also be a preferable condition for instance to actuate an inclusion packet of reagent which may be in a frangible capsule incorporated within the vessel.

In order to begin processing the fluid-sample by filtration, the blockages, clamps, or closures that have been applied to the fluid path to restrict flow are relieved. Fluid thereby can be permitted to flow from the vessel outlet and pass through the pathway to the filter-cartridge. It flows into the cartridge, displacing air that is within the inlet portion of the cartridge and continues to pass through the filtering means.

Filterable-constituent is captured within the cartridge, separated and removed by the filtering means. The filtrate, or portion of the fluid-sample processed by the filtering means with the filterable-constituent extracted, is discharged from the filter cartridge through its outlet.

The force causing the fluid-sample to flow through the device can involve simple gravity, with the conditional requirement that the components of the fluid pathway are oriented one to the next such that the fluid can flow. It has been described how the orientation of the vessel can be used to control, and prevent, fluid flow out of the vessel, for instance, by elevating the outlet so that it is above the level of the top of the fluid. Air alone in the vessel, when enabled to rise in the fluid so as to occlude the outlet, serves to block flow when there is no siphoning force to lift fluid in the pathway. To allow flow to precede, the vessel and the level of the fluid pathway components are reoriented to permit downward pull, including siphoning, of the fluid by gravity.

Whereas an unaided filtration of the fluid by gravity flow is a definitive attribute of the system, additional force can be applied to the fluid pathway in order to speed up the fluid flow and improve efficiency of the filtration process. For instance additional force can be a necessity in some cases in order to process the required volume of fluid-sample in a practical time; or to get a flow to proceed when resistance to flow gets too high due to accumulation of filterable-constituent on the filter means.

It is therefore another attribute of the inventive method that it is designed to enable additional external force to be applied, in particular, to the flexible vessel in order to push the fluid-sample out of the vessel and through the pathway. One practical embodiment can be by hand through simply squeezing on the outside of the containment vessel. The vessel thereby works like a squeeze-pump (with no incoming fluid). Additional embodiments can be mechanical implementations to similarly apply external pressure to the outside of the vessel in lieu of hand pressure. This is advantageous if the size of the vessel or the volume of fluid-sample is more than can be conveniently dealt with by hand. For instance, with limited resources, an alternative is to apply a weight to the vessel, even foot pressure. Other approaches offering mechanical advantage can further be implemented to put force on the vessel and pathway.

The valuable point is that the invention can be utilized effectively without obligate need of any ancillary tools, mechanical devices such as a pump or suction apparatus, or electrical power to operate such equipment. It will be appreciated that a fluid pumping mechanism clearly can be an embodiment practiced with the device and method, applied at the containment vessel, or optionally to a fluid conduit connecting the vessel to the filter cartridge.

Another purpose of applying external pressure on the device, including hand squeezing, is to push gas through the system. Air or gas bubbles may get into the fluid path. This can interfere with fluid flow; moreover air blockage has been described as one embodiment useful to intentionally prevent flow. It can be essential to have an additional force, more than gravity, in order to push fluid and drive the gas out of the path. This includes embodiment using pressure from fluid in the pathway as an approach to displace air out of the filter-cartridge, or to force air out through a gas-transfer vent as has been described.

Alternatively, another embodiment of the inventive design includes means to apply positive pressure on the fluid pathway to enable air/gas to be intentionally pushed through it. This usefully serves to clear fluid-sample from the pathway. In this case, after a volume of fluid-sample has been processed by filtration, the objective can be to purge fluid out of the pathway and especially the filter-cartridge. This is achieved by applying external pressure on the containment vessel such that air/gas remaining for instance in the vessel headspace is forced out and through the pathway. The positive pressure pushes the air/gas through the fluid pathway and purges the fluid ahead of it out of the pathway.

The analytical procedure for testing the filterable-constituent of the fluid-sample is conducted generally after the fluid-sample has been passed through the filter-cartridge and the filterable-constituent is separated and captured in the cartridge. However, procedures can be initiated at the onset of sample preparation, for example, by exposing the filterable-constituent to reagents introduced with the fluid-sample, or exposure to reagents that were incorporated into the fluid containment vessel.

In an embodiment of use, to perform analytical procedures, the filter-cartridge can be removed from the enclosed fluid pathway after the fluid containment vessel is no longer needed. This permits access to the pathway leading to the inlet 5 of the filter-cartridge, which is still protected by its enclosed housing. Additional fluids, reagents, and other substances, including culture media, needed to perform the analytical procedure on the filtered-constituent, may then be administered into the cartridge. Such substances employed can be reagents and growth-media, in liquid or dry form, as used for microbial assays or for other analytical tests of fluid-constituents.

Such administration is conducted for instance by positive-pressure injection into the cartridge, or by aspiration via the inlet with negative pressure applied at the cartridge outlet. The outlet cover or plug 8, which encloses, controls flow, and protects against external contamination at the distal end of the pathway, must be removed or set such that it allows fluid to pass through the filter-cartridge when fluids are administered to it and to allow discharged from the terminus of the pathway. Conversely, the outlet cover or plug can be replaced or reset such that it seals and protects the fluid-pathway's distal end and may hydraulically prevent further fluid movement in the pathway, when discharge from the outlet is not needed or wanted.

If the filter cartridge has been detached from the fluid pathway at its inlet, an additional closure can of course be applied to the inlet pathway of the filter-cartridge to provide protection of its contents and prevent leakage.

A filter cartridge removed from the sample-preparation fluid pathway is in an embodiment state suited for subsequent in situ analyses of the cartridge contents. The inlet and outlet of the filter-cartridge can be sealed and protected in further preferred embodiments. In the case of microbiological culture tests, an incubation stage is conducted to allow organisms to metabolize, multiply, and form colonies. It can be convenient to have the filter cartridge detached from other components of the device's fluid path at the analysis stage; albeit the cartridge inlet and outlet may be preferably covered and protected. As previously identified, a compact filter-cartridge of thin configuration can be a practical embodiment to wear close to one's body for body-heat incubation to facilitate the culture and growth of the organisms. Thereby the method has valuable utility when there is no incubation equipment or power available to operate incubators.

A particularly valuable application of the invention is to acquire the sample at the fluid source, then directly process it by passing it through the filter cartridge to promptly remove the filterable constituent, e.g. bacteria. The filter-cartridge can then be conveyed to the place where the analytical testing of the filtered contents of the cartridge is subsequently performed. This approach eliminates the complications and expense of transporting the entire fluid sample, which is not needed, to the test location.

This practice of filtering the sample at the point of acquisition, or shortly after, offers another major benefit: each organism captured in the filter subsequently produces but one colony of growth where it is trapped. This averts a threat to microbiological testing when the fluid-sample is not immediately analyzed. The risk is that the sample's composition changes over time due to proliferation of organisms retained in a fluid state; and the organisms may be altered by exposure to other constituents of the sample that also may be changing with time. Conventional tests require fluid samples be kept at low temperature to inhibit growth and composition changes and have limits to the time between sample acquisition and testing. Such issues and potential test errors are avoided by practicing the inventive method soon after the sample is acquired.

The system is inventive by enabling the fluid-sample to be filter-processed "in the field" at the time of or shortly after the sample acquisition and executed in a simple manner that prevents accidental sample contamination due to improper handling and exposure of the sample during the filtration process. The on-the-spot filter processing solves the problem of changes occurring within the sample during a holding period and the potential adverse effects on the sample-testing outcome.

What we claim is:

1. A device for fluid sample-preparation with an enclosed fluid pathway providing for the introduction of a fluid sample, transport of the fluid, extraction of filterable constituents from the fluid, and analysis of the extracted filterable constituents, having integrated components comprising:
    a flexible fluid containment vessel having expandable internal volume into which fluid sample is introduced through an opening in said vessel;
    a fluid outlet on said fluid containment vessel;
    an enclosed fluid conduit connecting the outlet of said vessel to an attached filter cartridge;
    the attached filter cartridge connected by the fluid conduit to said containment vessel through which said fluid sample is caused to pass;
    a filter contained within said filter cartridge which removes the constituent to be analyzed from the fluid passed through the filter cartridge;
    fluids, reagents, and/or analytics-related substances that carry out an analysis of the constituent to be analyzed within the filter cartridge to measure a presence or amount of a constituent of the fluid sample collected by said filter cartridge; and
    an outlet fluid pathway for discharge of fluid passed through the filter cartridge.

2. The device of claim 1 wherein the containment vessel has an opening receiving fluid that is sealable after the fluid sample is introduced.

3. The device of claim 1 wherein said fluid containment vessel is compressible.

4. The device of claim 1 employing a removable cover or closure to seal a tenninal point of fluid discharge from the outlet fluid pathway of said device.

5. The device of claim 1 wherein the filter cartridge is removable from the enclosed fluid conduit.

6. The device of claim 1 wherein the filter cartridge has a gas vent, through which gas is passed, or has an opening allowing escape of gas out of the filter cartridge so as to prevent air entering the filter cartridge from blocking the flow of fluid through said filter cartridge.

7. The device of claim 1 wherein fluid flow through the fluid pathway are controlled by valves or closure mechanisms that regulate flow of fluid.

8. The device of claim 1 wherein said containment vessel contains inclusions, reagents or substances incorporated inside the fluid containment vessel to aid sample preparation or analysis.

9. The device of claim 1 further comprising an enclosed fluid collection vessel attached at a distal end to receive and retain fluid discharged from the outlet fluid pathway.

* * * * *